(12) United States Patent
Campbell et al.

(10) Patent No.: US 7,338,473 B2
(45) Date of Patent: *Mar. 4, 2008

(54) PNEUMOSEAL TROCAR ARRANGEMENT

(75) Inventors: Michael J. Campbell, Louisville, KY (US); Donald N. Halgren, Manchester, MA (US); George A. J. Hartman, Waynesville, OH (US); Ken Parker, Centerville, OH (US); Jack B. Stubbs, Waynesville, OH (US); Ronald J. Thompson, Ft Thomas, KY (US)

(73) Assignee: SurgiQuest, Incorporated, Orange, CT (US)

( * ) Notice: Subject to any disclaimer, the term of this patent is extended or adjusted under 35 U.S.C. 154(b) by 335 days.

This patent is subject to a terminal disclaimer.

(21) Appl. No.: 10/776,923

(22) Filed: Feb. 11, 2004

(65) Prior Publication Data

US 2005/0004512 A1    Jan. 6, 2005

Related U.S. Application Data

(63) Continuation-in-part of application No. 10/739,872, filed on Dec. 18, 2003, now Pat. No. 7,285,112, which is a continuation-in-part of application No. 10/441,149, filed on May 17, 2003, now Pat. No. 7,182,752.

(60) Provisional application No. 60/461,149, filed on Apr. 8, 2003.

(51) Int. Cl.
*A61M 5/178* (2006.01)

(52) U.S. Cl. .............. 604/167.01; 604/23; 604/26; 604/500; 604/506; 604/164.01; 606/167

(58) Field of Classification Search ............ 604/23–26, 604/35, 43–45, 506, 264, 272, 500, 507, 604/164.01, 164.02, 167.01, 167.02, 167.03, 604/167.04, 167.05, 167.06; 606/167
See application file for complete search history.

(56) References Cited

U.S. PATENT DOCUMENTS

| 4,184,510 A | 1/1980 | Murry et al. |
| 4,535,773 A | 8/1985 | Yoom |

(Continued)

FOREIGN PATENT DOCUMENTS

DE    195 23 685 A1    1/1997

(Continued)

OTHER PUBLICATIONS

"Infant Flow System" from www.eme-med.co.uk.

(Continued)

*Primary Examiner*—Kevin C. Sirmons
*Assistant Examiner*—Laura C. Schell
(74) *Attorney, Agent, or Firm*—Scott D. Wofsy; Edwards Angell Palmer & Dodge LLP

(57) ABSTRACT

A cannula assembly for the maintenance of an operative pneumoperitoneum in a patient comprising an elongated cannula having a proximal end and a distal end. A removable valve is securely arranged in the proximal end of the cannula to provide a seal and minimize the escape of gas introduced into the patient's pneumoperitoneum when an operative instrument is passed therethrough.

9 Claims, 3 Drawing Sheets

U.S. PATENT DOCUMENTS

| | | | |
|---|---|---|---|
| 4,735,603 A * | 4/1988 | Goodson et al. | 604/21 |
| 4,792,335 A | 12/1988 | Goosen et al. | |
| 4,869,717 A | 9/1989 | Adair | |
| 5,013,294 A | 5/1991 | Baier | |
| 5,190,068 A | 3/1993 | Philbin | |
| 5,203,767 A * | 4/1993 | Cloyd | 604/11 |
| 5,300,047 A | 4/1994 | Beurrier | |
| 5,312,351 A | 5/1994 | Gerrone | |
| 5,328,458 A | 7/1994 | Sekino et al. | |
| 5,545,150 A | 8/1996 | Danks et al. | |
| 5,800,381 A | 9/1998 | Ognier | |
| 5,849,005 A | 12/1998 | Garrison et al. | |
| 5,916,198 A | 6/1999 | Dillow | |
| 6,042,573 A | 3/2000 | Lucey | |
| 6,162,196 A | 12/2000 | Hart et al. | |
| 6,217,555 B1 * | 4/2001 | Hart et al. | 604/167.01 |
| 6,228,058 B1 | 5/2001 | Dennis et al. | |
| 6,253,766 B1 | 7/2001 | Niles et al. | |
| 6,299,592 B1 | 10/2001 | Zander | |
| 6,309,382 B1 * | 10/2001 | Garrison et al. | 606/1 |
| 6,482,181 B1 | 11/2002 | Racenet et al. | |
| 6,497,687 B1 | 12/2002 | Blanco | |
| 6,508,859 B1 | 1/2003 | Zia et al. | |
| 6,544,210 B1 * | 4/2003 | Trudel et al. | 604/26 |
| 6,645,197 B2 * | 11/2003 | Garrison et al. | 606/1 |
| 6,905,489 B2 * | 6/2005 | Mantell et al. | 604/506 |
| 6,942,671 B1 * | 9/2005 | Smith | 606/108 |
| 2002/0120226 A1 | 8/2002 | Beck | |
| 2002/0128603 A1 | 9/2002 | Booth et al. | |
| 2002/0161387 A1 | 10/2002 | Blanco | |
| 2003/0040711 A1 | 2/2003 | Racenet et al. | |
| 2003/0045834 A1 | 3/2003 | Wing et al. | |
| 2004/0199121 A1 | 10/2004 | Wenchell et al. | |
| 2006/0079925 A1 * | 4/2006 | Kerr | 606/198 |

FOREIGN PATENT DOCUMENTS

| | | |
|---|---|---|
| EP | 0 323 018 B1 | 6/1993 |
| EP | 1 188 415 A | 3/2002 |
| WO | WO 96/01132 A | 1/1996 |
| WO | WO 00/37134 | 6/2000 |
| WO | WO 01/91653 A | 12/2001 |

OTHER PUBLICATIONS

"Air Jets and Nozzles" from www.exair.com.
Invitation to Pay Additional Fees and Annex to Form PCT/ISA/206 Communication Relating to the Results of the Partial International Search.

* cited by examiner

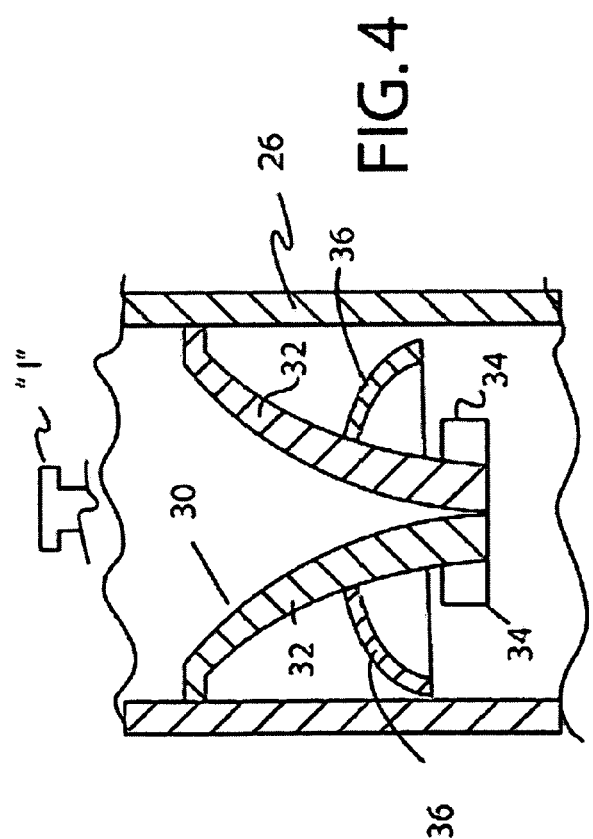
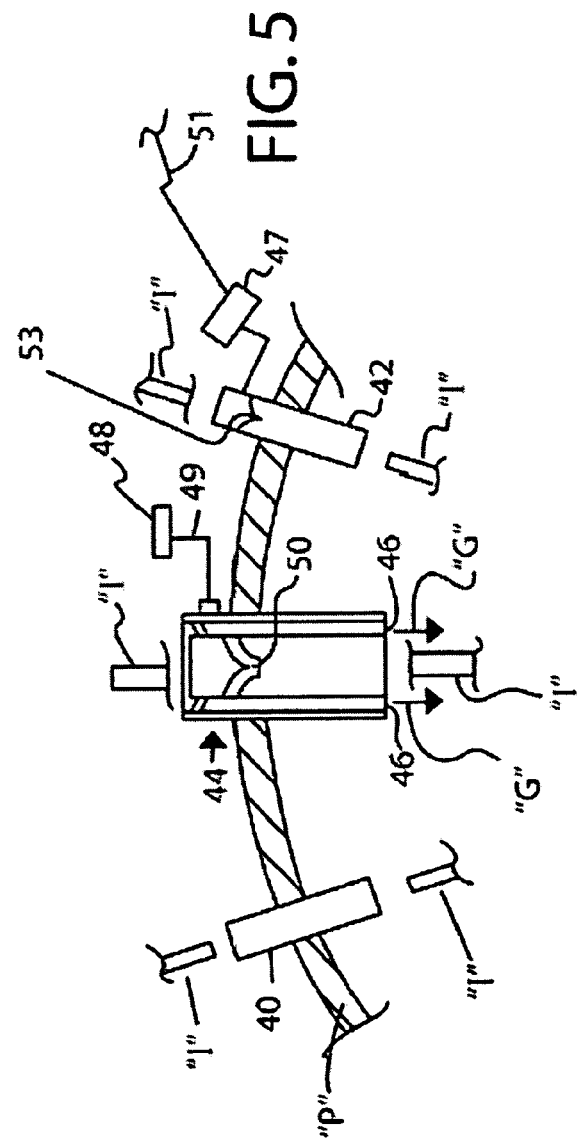

PNEUMOSEAL TROCAR ARRANGEMENT

This application is a continuation-in-part application of our U.S. patent application Ser. No. 10/739,872, filed 18 Dec. 2003, now U.S. Pat. No. 7,285,112, which is a continuation-in-part application of U.S. patent application Ser. No. 10/441,149 filed 17 of May 2003, now U.S. Pat. No. 7,182,752, which is based upon and incorporates herein provisional patent application Ser. No. 60/461,149 filed 8 of Apr. 2003, each of which are incorporated herein by reference in their entirety.

BACKGROUND OF THE INVENTION

1. Field of the Invention

This invention relates to methods and apparatus of trocar devices and more specifically, arrangements to increase the efficiency of a pneumoseal (no seal) cannula when used in conjunction with a multitude of other various different ID sized cannulae.

2. Prior Art

The primary goal of cannula seals for laparoscopic, or minimally invasive surgery is to maintain gaseous distention of the abdominal cavity adequately for an operative pneumoperitoneum. An operative pneumoperitoneum is the maintenance of adequate vision and access to anatomic structures for surgical manipulation despite the frequent exchange of instruments through those cannula seals. As described in our above identified co-pending U.S. patent applications relating to an active pneumoseal, an infused distention gas is directly borne through a trocar arrangement to create a non-mechanical seal and to maintain an operative pneumoperitoneum in a patient being operated upon. This is a viable alternative to existing seal technology. A prototype pneumoseal trocar arrangement has displayed a surprising reserve capacity in both bench and animal lab testing. Results from these tests showed that the pneumoseal (no mechanical seal) cannula was able to maintain an operative pneumoperitoneum despite a free loss of distention gas through a multitude of other medium bore (5 mm) non-sealed cannulas arranged in a test situation. In fact, three 5 mm non-sealed cannulas and a 12 mm pneumoseal were utilized while still maintaining an operative pneumoseal with the pneumoseal trocar of the present invention. (This is like operating through ordinary soda straws if used in conjunction with a pneumoseal 12 mm cannula.)

The efficiency of any cannula seal system in a normal operative environment can best be described as a function of three variables: 1) the volume of distention gas infused into the operative pneumoperitoneum; 2) the volume of gas lost from the operative pneumoperitoneum; 3) the maintenance of the operative pneumoperitoneum adequate for uninterrupted surgical tasks. The pneumoseal arrangements of the present invention utilize a high flow of distention gas in a large bore cannula to create a wall of air preferably at an angle with respect to the longitudinal axis of the cannula. In conventional mechanical seal technology, a low flow of distention gas is insufflated into the patient through a separate cannula, which gas used to maintain an operative pneumoperitoneum. Medical instruments for the operative procedure are introduced into the patient through a trocar, and each singular instrument must be passed through a valve like mechanical seal such as a duck bill valve, a slit-like valve or a flap valve, in an attempt to maintain the pneumperitoneum. Any gas lost from the operative pneumoperitoneum is therefore detrimental to the operation, and must be addressed (re-introduced) before surgery can resume. In a typical laparoscopic surgical procedure, many different cannulae are used. A partial obstruction of the outflow of distending gas from the pneumoperitoneum in one or all of the cannulae used would increase the overall efficiency of the cannula system. The pneumoseal technology of the present invention provides this partial obstruction while maintaining an adequate operative pneumoperitoneum. Such a partial obstruction typically would fail using current mechanical seal technology. In the mechanical seal technology of the prior art, any loss of distending gas completely destroys the operative pneumoperitoneum. In fact, currently available cannulas have a dual mechanical seal to maintain an operative pneumoperitoneum. The seal is so critical that a defect of 1 mm or less in any part of the system is enough to render the pneumoperitoneum inoperative.

Currently available airtight cannulae use two valves per cannula to insure the maintenance of an operative pneumoperitoneum. The proximal "universal seal" of the prior art is shown in Applied Medical Corporation patents '553 and '850, with a floating valve to completely seal around round instruments from 5 mm to 12 mm outside diameter. The introduction of an instrument through these prior art seals decreases the efficiency of the distal airtight seal, whether the seal is a "flap" valve or a "duck bill" valve. This is because each of these types of distal prior art valves do not conform to the complete outer circumference of any instrument introduced through that valve. Without an instrument in the cannula channel, the proximal valve of the prior art maintains a 4 mm opening. The operative pneumoperitoneum is maintained by the airtight flap valve or duckbill valve in the channel of the cannula. The efficiency of the seal is somewhat lost because the air input in these cannulas of the prior art is proximal to the valve. To increase gas in the distending pneumoperitoneum, the valve must be opened. If the gas input were positioned distal to the mechanical "flap" or "duck bill" valves, as accomplished by the present invention, the input gas would distend the operative pneumoperitoneum and close the mechanical valve with upward or "backward" pressure.

The efficiency of any pressurized space such as the operative pneumoperitoneum depends upon the gas input and gas loss. Current laparoscopic insufflation equipment interposes an electrically controlled modulating system between the high pressure/high flow gas input and the patient. Only one tube connects the insufflation equipment and the operative pneumoperitoneum, for this single tube both supplies insufflation gas and monitors the pressure within the pneumoperitoneum. Currently, the one tube system operates on a pulsitile node where the gas is insufflated for six seconds and paused for two seconds. The pressure node is to be able to measure the back pressure in the single tube, an indirect measurement of the pressure in the operative pneumoperitoneum. This arrangement decreases the efficiency of the pressurized space, for the inflow of gas to supply and support the pneumoperitoneum is only available 70 to 80% of the time. A more efficient system would be one aspect of the present invention wherein a two tube arrangement having one tube or cannula to supply the pneumoperitoneum is a dedicated supply line and the second tube is a dedicated pressure monitoring line. In such a two line system of the present invention, the input efficiency would rise to 100% of gas insufflation. In addition, the pressure measuring line would be constant, not intermittent, and therefore pressure measurements would occur in real time.

In a further aspect of the present invention of the two line system, an input gas supply line and an output, intra-abdominal pressure sensing line may be connected with a mechanical modulating device without having to rely upon the current electrical control of gas input of the prior art.

Also, with a two line system of the present invention, the pressure measuring line may be connected to a double lumen cannula, or alternatively, to a separate pneumoperitoneum measuring dedicated cannula, or alternatively, again for example, the pressure measuring line may be connected to a free standing trans-abdominally placed, intra-peritoneal sensor. Either of these alternative preferred embodiments will permit both continuous direct intra-abdominal pressure measurements through one line, and the continuous direct insufflation of gas to the pneumoperitoneum, to increase the gas input to 100% efficiency.

BRIEF SUMMARY OF THE PRESENT INVENTION

In a first aspect of the present invention, by positioning a partial obstruction in the outflow path of gas from the pneumoseal of the present invention, the volume of lost gas is reduced by the back pressure. The partial obstruction could be placed anywhere in the cannula, as long as it is proximal to the inflow of gas for the pnuemoseal and the operative pneumoperitoneum. In addition, the active high pressure and high volume of distending gas could be used to increase or decrease the size of the partial obstruction. The partial obstruction of the outflow of gas could be a design feature of only one large bore cannula, several large bore cannulas, or all of the cannulas used in a surgical procedure. Once again, the advantage of a partial obstruction would be to increase the efficiency of a multiple cannula system by decreasing the loss of distension gas from the pneumoseal and the operative pneumoperitoneum. Such partial obstruction of a current dual mechanical valve cannula of the prior art would be surgically inappropriate because it would not be airtight.

In a closed pressurized system such as an operative pneumoperitoneum, gas pressure can be measured at any anatomic location. In an open pressurized system, like the pneumoseal system, the pressure maintaining the operative pneumoperitoneum can only be measured within the pneumoperitoneum. This is because in an open pressurized system, the pressure in the inflow, outflow or combined gas streams is only representative of the static peritoneum pressure when measured at some point beyond the distal end of the cannula and within the peritoneum. Outflow of gas through the cannula can be reduced by using a partial obstruction as recited hereinabove. If the outflow of gas were not interrupted by the inflow of gas, the outflow of gas would only be constrained by the flow characteristics of the open cannula and a large flow volume would occur. If the outflowing gas encounters a shaped inflow of high pressure gas within the cannula body, the outflow gas flow characteristics are changed dramatically and the volume of outflowing gas is greatly reduced. This principle is the basis of the pneumoseal cannula. In addition, there would be upward flow gas through the cannula. This upward flow could be used to increase the efficiency of a partial obstruction, increasing the overall efficiency of the "no seal" cannula of the present invention, even when utilizing other components of a multiple cannula system with the patient.

The present invention, in one aspect increases the efficiency of the pneumoseal cannula by introducing a partial obstruction within the cannula proximal to the air input orifice. Such a cannula of the present invention may be effectively utilized with a plurality of cannulas that are non-obstructed, partially obstructed, or fully obstructed to increase the efficiency of the pneumoseal system of cannulas, which may be measured by the maintenance of an adequately stable operative pneumoperitoneum. A partial obstruction may be made by using an active gas inflow to urge the walls of the partial obstruction to decrease the outflow of gas, by compression on those walls even to the point of creating a total obstruction. Total obstruction created by a series of fins to baffle the air flow and harness lateral closure forces upon the walls of that valve.

In a further aspect of the present invention, the operative instrument is arranged to provide the inflow of gas within its particular cannula to effect the pneumseal within the patient. Such an instrument in one embodiment would have an annular collar functioning as a manifold, directing a flow of input gas from the collar, the gas being received from a pressurized source through a flexible hose to such collar on a peripheral portion of that instrument. In a further embodiment, such operative instrument has a proximal fitting to releasably receive the attachment of a gas inflow supply conduit. Channels within the proximal end of the instrument would direct the inflow gas to outlet ports at a more distal location or locations on the instrument for introduction into the patient to provide the operative pneumoperitoneum. The introduction of such inflow gas would be distal to any valve arrangement within the cannula assembly in which the instrument is extending.

The invention thus comprises a cannula assembly for the maintenance of an operative pneumoperitoneum in a patient comprising an elongated cannula having a proximal end and a distal end. A valve is preferably securely arranged within, on or adjacent the proximal end of the cannula to provide a tight seal and minimize the escape of gas which has been introduced into the patient's pneumoperitoneum when an operative instrument is passed therethrough. The valve may comprise an inner portion of a proximal cap which is fixed or removably attachable to the proximal end of the cannula. The valve assembly may have a compressible O-ring thereon to provide a further seal of the cap to the cannula. The valve may have a plurality of fluid flow directing fins thereon to direct any backflow of gas to tighten the sealing effect of the valve. The valve may have a distal underside with a pocket arrangement thereon to capture any backflowing gas and create a more efficient seal by the valve in the cannula.

In a further aspect of the present invention, the operative instrument itself may preferably have at least one gaseous fluid discharge port arranged thereon to permit the introduction of distension gas through the instrument and into the patient, and distal to any seal at or near the proximal end of the trocar. The gaseous port in one preferred embodiment may comprise a collar disposed about at least a peripheral portion of the instrument, the collar having at least one discharge jet thereon to provide pressurized gas from a controlled pressure source into the patient's abdomen.

The invention may also comprise a method of maintaining an operative pneumoperitoneum in a patient undergoing a surgical procedure comprising one or more of the following steps: introducing a trocar through a portion of an abdominal wall of the patient; introducing an operative surgical instrument through a lumen in the trocar; and introducing a pressurized gas from a controlled pressure source into the patient through a passageway between the surgical instrument and a wall of the lumen in the trocar, introducing the pressurized gas into the passageway between the surgical instrument and a wall of the lumen in the trocar via at least one port in the trocar or introducing the pressurized gas into the passageway between the surgical instrument and a wall of the lumen in the trocar via at least one port in a wall portion of the surgical instrument; introducing at least one cannula into an abdominal wall portion of the patient; introducing an operative surgical instrument through the at least one cannula to permit simultaneous operative function with the trocar as the trocar is caused to introduce distension gas into the patient. The method also includes the gas introducing trocar having a plurality of medically operative instruments extending therethrough simultaneously. The cannula preferably has an open bore extending therethrough to permit operative instruments to work therethrough without a mechanical seal such as a valve.

BRIEF DESCRIPTION OF THE DRAWINGS

The objects and advantages of the present invention will become more apparent when viewed in conjunction with the following drawings in which:

FIG. 4 is a side elevational view of a cannula with a closure valve arranged therein;

FIG. 5 is a cross-sectional view of a plurality of cannulae arranged within a patient's abdomen, one of the cannula comprising a pneumoseal cannula of the present invention;

DETAILED DESCRIPTION OF THE PREFERRED EMBODIMENTS

Figure 1:
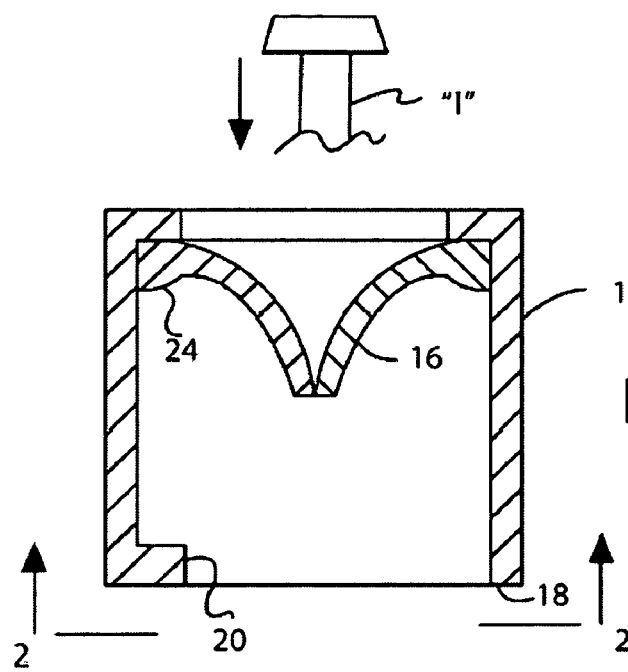
FIG. 1 is a side elevational view, in section of a lockable proximal cap for a trocar, with a valve arranged within that proximal cap.
Figure 2:
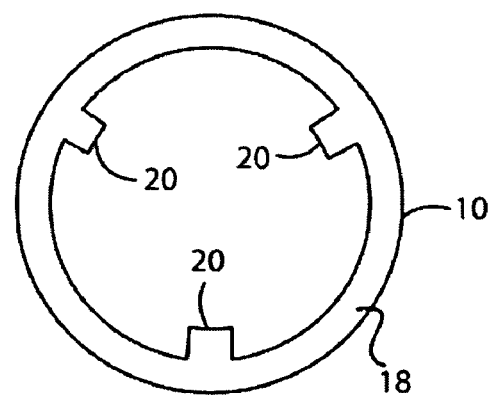
FIG. 2 is a view taken along the lines 2-2 of FIG. 1.
Figure 3:
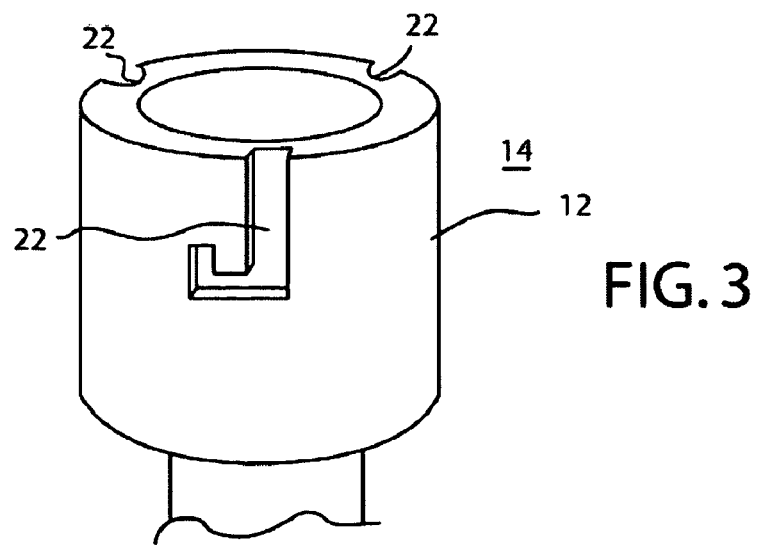
FIG. 3 is a perspective view of the proximal end of a cannula arranged for receipt of the proximal cap shown in FIG. 1.

The present invention comprises in a first aspect thereof, a proximal cap 10, as shown in FIG. 1, arranged for securable attachment to the proximal end of a cannula 12, which comprises a trocar assembly 14 of the present invention. The cap 10 may have a flexible flap, slit or "duckbill" type valve 16 fitted therein. The cap 10 is preferably of cylindrical shape and has a distal edge 18. A plurality of inwardly directed spurs 20 are arranged within the distal edge 18 of the cap 10, as shown in FIGS. 1 and 2. The spurs 20 are circumferentially spaced so as to mate with and lock into a plurality of receiving grooves 22 in a "bayonet" manner on the proximal periphery of the cannula 12, as represented in FIG. 3. An operative surgical instrument "I" would then be introduced through this proximal valve 16 on the cannula 12. The valve 16 may in a further embodiment, have a soft compressable "O" ring 24 unitarily arranged about its proximal periphery, as represented in FIG. 1. The O-ring 24 would function to further seal the valve when the cap 10 is mated onto the proximal end of the cannula 12.

In a further aspect of the present invention, the sealing of the instrument within a cannula 26 is represented by a flap or duckbill valve 30 shown in FIG. 4. Such a valve 30 has flexible web portions 32 between which an instrument "I" will be manipulated. To maintain the optimum seal between the valve 30 and an instrument "I" extending therethrough, the distal underside of the web portions 32 have radially arranged gas back flow directing fins 34 attached thereon, as shown in FIG. 4. Such fins 34 direct backflow gas into an arrangement of pockets 36, also arranged on the distal underside of the web portions 32 of the valve 30. The fins 34 direct air/gas into and against the web 32 of the valve 30 to further block the escape of gas introduced distally into the pneuperitoneum as identified in this patent application and also the aforementioned patent applications describing other aspects of the present invention, incorporated herein by reference.

An aspect of the present invention is again represented, as shown in FIG. 5, wherein a plurality of standard cannulae 40 and 42 such as for example, 5 mm or 12 mm cannulae are shown with an operative surgical instrument "I" extending therethrough. A pneumoseal trocar arrangement 44 of the present invention is also shown with an operative instrument "I" extending therethrough into the abdominal portion of a patient "P". The trocar arrangement 44 introduces a controlled pressurized gas 'G" from a distal location 46 on that trocar arrangement 44, supplied from a controlled gas source 48 through a supply conduit 49. The pneumoseal trocar arrangement 44 is so efficient that the conventional cannulae 40 and 42, (such as for example, a 5 mm, a 10 mm or a 12 mm cannula), may be utilized concurrently therewith, without loss of the operative pneumoperitoneum in the patient P.

A further aspect of the present invention comprises utilizing one of more of the conventional cannulae 40 and/or 42 (a 5, 10 or 12 mm cannula) with a pressure sensor 47 thereassociated. Such a sensor 47 may be in communication with the controlled gas source 48 through a proper connecting circuit 51. Such a conventional cannula 42 may also have a valve 53 therewithin, as represented in FIG. 5 to more accurately determine the backpressure within the patient "P". It is to be noted that the trocar 44 in one embodiment does not need a proximal valve such as proximal valve 50 to be effective.

A slit or duckbill valve 50 is also shown within the interior passageway of the trocar arrangement 44, which valve 50 is disposed proximal of the gas discharge ports 46 to provide the sealing in this embodiment, in which embodiment, a flap or slit type valve is actually utilized.

Figure 6:
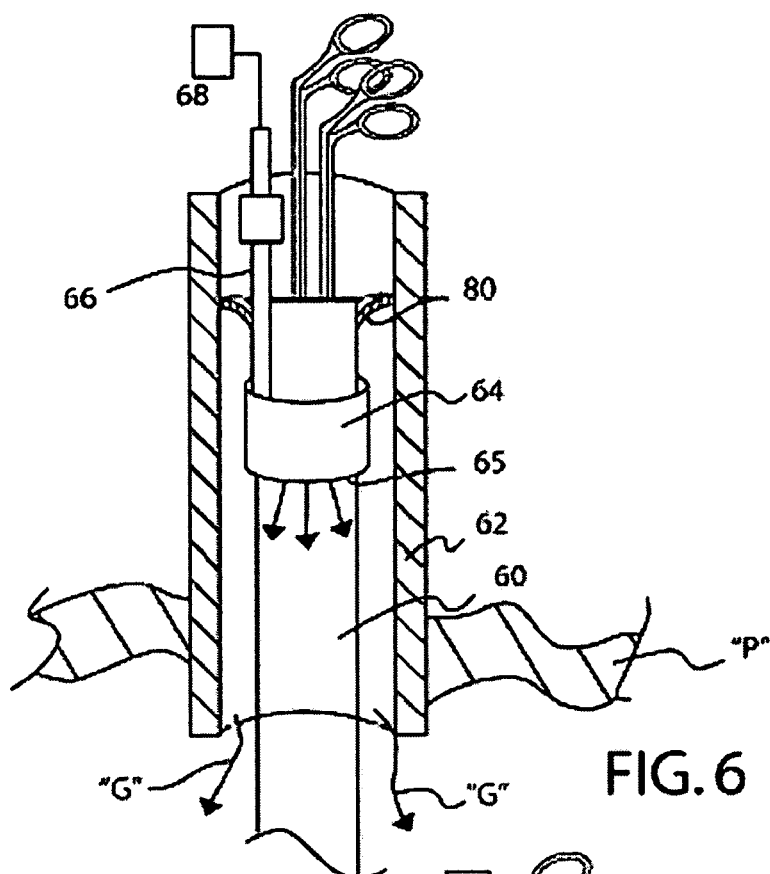
FIG. 6 is a side elevational view of a cannula with an operative pneumo-instrument for providing its own gas introduction into the patient.
Figure 7:
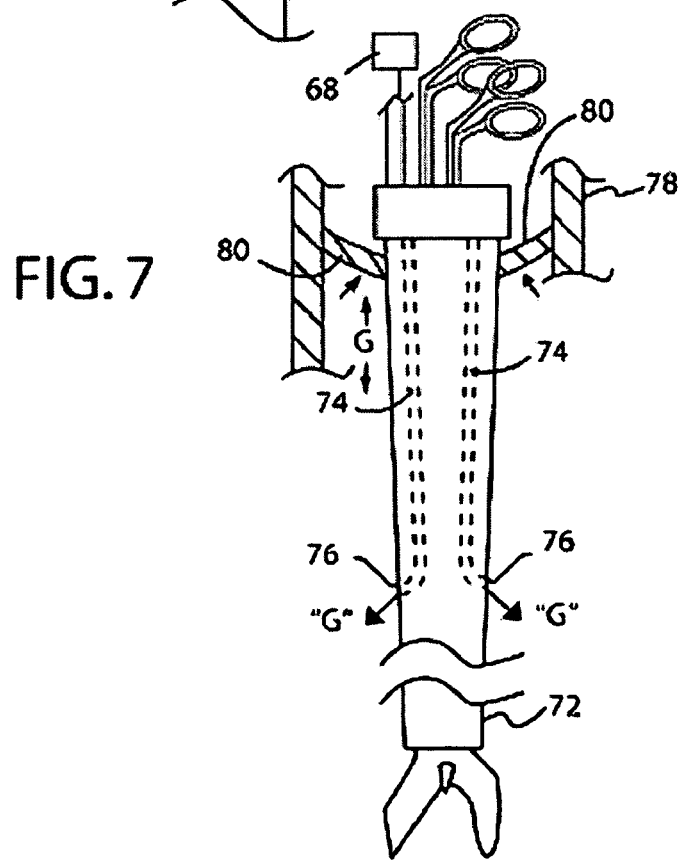
FIG. 7 is a further embodiment of the invention shown in FIG. 6.

A further aspect of the present invention is represented in FIG. 6, wherein an operative surgical instrument 60 is shown extending through a trocar 62. Inflow gas for the pneumoperitoneum is introduced via the surgical instrument 60. A collar 64 in one preferred embodiment, is arranged around at least at a longitudinal mid portion of the periphery of the instrument 60, as represented in FIG. 6. The collar 64 in this preferred embodiment is in fluid communication with a pressurized fluid supply conduit 66. The conduit 66 is connected to controlled fluid pressure source 68. Pressurized fluid such as for example air or carbon dioxide is introduced into the collar 64 and exits therefrom through discharge ports 65 in the collar 64 and thence into the annular channel between the instrument 60 and the inside of the trocar 62 and is thus introduced into the patient "P". A slit, duckbill or like valve 80 in a further embodiment thereof, may arranged proximal to the collar 64 within the trocar 62 to minimize the escape of gas introduced into the pneumoperitoneum through the collar 64.

A further embodiment of the operative instrument 72 comprises an arrangement of channels 74 within the proximal portion of that instrument 72 leading to discharge ports 76, all displaceably arranged within a trocar 78. A flexible valve 80 may be disposed within the trocar 78 to help block escape of gas "G" introduced into the pneumoperitoneum. The pressure of such gas "G acts to press the body of the proximally disposed flexible valve 80 against the body of such instrument 60 or 72 in an improved manner of sealing such instrument within the trocar 62 and 78. Such valving 80 in certain aspects of the present invention may be unnecessary because of the gas flow jetting distally of the trocar assemblies 62 and 78 effect its own seal around any shaped instrument "I" extending therethrough. Thus, such instrument need not be circular in cross-section, nor such instrument be utilized in a sin manner, but may be utilized as identified in our aforementioned applications, in combination with several laparoscopic instruments through a single trocar. Such combination may also be represented in FIG. 5 wherein one cannula 42 may be utilized for example, such as a 5 mm or a 10 mm cannula, for pressure monitoring and feedback through its control 47, while the trocar 44 may provide the air inflow into the patient "P", the gas "G" also functioning as the instrument seal arrangement for the instrument or instruments "I" extending manipulatively therethrough.

Thus what has been shown is a unique arrangement for the maintenance of an operative pneumoperitoneum by a valve arrangement for sealing one or more round or non-round surgical instruments working through a pneumoseal cannula while a wall of gas functioning as an instrument seal and as a pressure source for the pneumoperitoneum, and while other surgical instruments may be operating simultaneously through standard cannulae without the need for such pressure loss concerns.

We claim:

1. A method of maintaining an operative pneumoperitoneum in a patient undergoing a surgical procedure comprising the steps of:
   introducing a trocar through a portion of an abdominal wall of a patient;
   introducing a surgical instrument through a lumen in the trocar;
   introducing a pressurized gas from a controlled pressure source into the surgical instrument;
   directing the pressurized gas from the surgical instrument into the patient through a passageway between the surgical instrument and a wall of the lumen in the trocar, the pressurized gas from the surgical instrument forming a gas seal around the surgical instrument within the lumen of the trocar so as to directly contact the surgical instrument, while said pressurized gas simultaneously maintains an operative pneumoperitoneum in the patient by preventing a loss of pressurized gas from the pneumoperitoneum through the lumen in the trocar; and
   monitoring the pneumoperitoneum of the patient to provide feedback for maintaining the operative pneumoperitoneum.

2. The method as recited in claim 1, wherein the step of directing pressurized gas from the surgical instrument into the patient through a passageway between the surgical instrument and a wall of the lumen in the trocar involves directing a flow of pressurized gas through at least one port in a wall portion of the surgical instrument.

3. The method as recited in claim 1, further including the steps of: introducing a first cannula into an abdominal wall portion of the patient; and introducing at least one operative surgical instrument through the first cannula to permit simultaneous operative function with the trocar.

4. The method as recited in claim 3, further including the steps of: introducing a second cannula into the patient; and wherein the step of monitoring the pneumoperitoneum of the patient occurs through the second cannula.

5. The method as recited in claim 1, wherein the step of directing the pressurized gas from the surgical instrument into the patient involves directing a flow of pressurized gas into the lumen of the trocar at a location distal to any valve arrangement within the trocar.

6. A method of maintaining an operative pneumoperitoneum in a patient undergoing a surgical procedure comprising the steps of:
   introducing a trocar through a portion of an abdominal wall of a patient at a first site;
   introducing at least one surgical instrument through a lumen in the trocar;
   introducing a pressurized gas from a controlled pressure source into the at least one surgical instrument;
   directing the pressurized gas from the at least one surgical instrument into the patient through a gas passageway between the at least one surgical instrument and a wall of the lumen in the trocar so as to directly contact the at least one surgical instrument, the pressurized gas forming a gas seal around the at least one surgical instrument within the lumen in the trocar, while said pressurized gas simultaneously maintains the operative pneumoperitoneum by preventing a loss of pressurized gas from the pneumoperitoneum through the lumen in the trocar;
   introducing a cannula through the abdominal wall of the patient at a second site;
   monitoring gas pressure within the abdomen of the patient through the cannula; and
   controlling gas pressure within the abdomen of the patient based upon feedback received from the cannula so as to maintain the operative pneumoperitoneum with the pressurized gas from the at least one surgical instrument.

7. The method as recited in claim 6, wherein the trocar and the cannula are arranged in operative communication with one another to controllably balance pressurized gas introduced into the patient.

8. The method as recited in claim 6, wherein the trocar has a plurality of surgical instruments extending therethrough simultaneously.

9. The method as recited in claim 6, wherein the cannula has an open bore extending therethrough to permit operative instruments therethrough.

* * * * *